(12) United States Patent
Stanford et al.

(10) Patent No.: US 11,197,783 B2
(45) Date of Patent: Dec. 14, 2021

(54) TWO-PART BANDAGE WITH REPLACEABLE WOUND COVERING PORTION

(71) Applicants: Amanda J. Stanford, Northville, MI (US); Patrick G. Stack, Northville, MI (US)

(72) Inventors: Amanda J. Stanford, Northville, MI (US); Patrick G. Stack, Northville, MI (US)

(*) Notice: Subject to any disclaimer, the term of this patent is extended or adjusted under 35 U.S.C. 154(b) by 477 days.

(21) Appl. No.: 15/973,150

(22) Filed: May 7, 2018

(65) Prior Publication Data

US 2018/0250169 A1    Sep. 6, 2018

Related U.S. Application Data

(63) Continuation-in-part of application No. 14/664,716, filed on Mar. 20, 2015, now abandoned.

(51) Int. Cl.
*A61F 13/00* (2006.01)
*A61F 13/02* (2006.01)

(52) U.S. Cl.
CPC .... *A61F 13/0243* (2013.01); *A61F 13/00059* (2013.01); *A61F 13/0206* (2013.01); *A61F 2013/0057* (2013.01); *A61F 2013/00102* (2013.01); *A61F 2013/00153* (2013.01); *A61F 2013/00182* (2013.01); *A61F 2013/00217* (2013.01); *A61F 2013/00251* (2013.01); *A61F 2013/00557* (2013.01)

(58) Field of Classification Search
CPC .... A61F 2013/00102; A61F 2013/0053; A61F 2013/00153; A61F 2013/00182; A61F 2013/00217; A61F 2013/00251; A61F 2013/00557; A61F 2013/00157; A61F 2013/53925
USPC ................................ D24/189; 602/41–59
See application file for complete search history.

(56) References Cited

U.S. PATENT DOCUMENTS 2,905,174 A * 9/1959 Smith ................. A61F 13/0206
602/42
3,073,303 A * 1/1963 Schaar .................... C09J 7/255
602/59

(Continued)

OTHER PUBLICATIONS

Bump-definition of bump by The Free Dictionary https:www.thefreedictionary.com/bump (Year: 2021).*

(Continued)

*Primary Examiner* — Kim M Lewis
(74) *Attorney, Agent, or Firm* — Mitchell Law PLLC; Matthew W. Mitchell

(57) ABSTRACT

A two-piece bandage is useful for treating wound on a patient. The bandage includes a boundary portion including a bottom surface comprising adhesive for attaching the boundary portion to skin of a patient, an open window in the middle of the boundary portion permitting one to view a wound through the open window, and a top surface. The top surface includes a first portion of the top surface surrounding the open window including a flat surface and a second portion of the top surface including an uneven surface. The bandage further includes a plurality of replaceable wound covering portions, each replaceable wound covering portion comprising a padded section comprising a material to dress the wound.

5 Claims, 11 Drawing Sheets

(56) References Cited

U.S. PATENT DOCUMENTS

| | | | | |
|---|---|---|---|---|
| 3,885,559 | A | * | 5/1975 | Economou .......... A61F 13/0203 <br> 602/55 |
| 4,612,230 | A | * | 9/1986 | Liland .................. A61B 17/085 <br> 428/167 |
| 5,086,763 | A | * | 2/1992 | Hathman ............ A61F 13/0246 <br> 128/887 |
| 5,637,080 | A | * | 6/1997 | Geng .................... A61F 13/023 <br> 602/42 |
| 6,689,931 | B2 | * | 2/2004 | Etheredge, III .... A61F 13/0206 <br> 602/41 |
| D530,015 | S | * | 10/2006 | Douglas ............... A61B 17/085 <br> D24/189 |
| 7,205,449 | B2 | * | 4/2007 | Levin .................. A61F 13/0203 <br> 602/41 |
| D629,114 | S | * | 12/2010 | Masini ................. A61F 15/008 <br> D24/189 |
| 8,252,971 | B2 | * | 8/2012 | Aali ................... A61F 13/00072 <br> 602/56 |
| 8,277,940 | B2 | * | 10/2012 | Desiderio ........... A61F 13/0283 <br> 156/145 |
| 8,530,720 | B2 | * | 9/2013 | Freer .................... A61F 13/0233 <br> 602/43 |
| 2010/0010458 | A1 | * | 1/2010 | Sherman ............... A61F 13/023 <br> 604/307 |
| 2011/0015557 | A1 | * | 1/2011 | Aali ...................... A61F 15/008 <br> 602/56 |
| 2014/0323941 | A1 | * | 10/2014 | Lee ......................... A61L 15/60 <br> 602/54 |
| 2015/0133844 | A1 | * | 5/2015 | Montulet ............ A61F 13/0259 <br> 602/44 |
| 2016/0270968 | A1 | * | 9/2016 | Stanford ............. A61F 13/0236 |

OTHER PUBLICATIONS

Ridge-definition of bump by The Free Dictionary https:www.thefreedictionary.com/ridge (Year: 2021).*

\* cited by examiner

TWO-PART BANDAGE WITH REPLACEABLE WOUND COVERING PORTION

CROSS REFERENCE TO RELATED APPLICATIONS

This disclosure is a continuation in part of U.S. application Ser. No. 14/664,716 filed on Mar. 20, 2015, which is hereby incorporated by reference.

TECHNICAL FIELD

This disclosure is related to a bandage used in medical care. In particular, the disclosure is related to a two-part bandage including a first boundary portion adhered to the skin of the patient and including a window and a second wound covering portion covering the window and adhering to the boundary portion.

BACKGROUND

The statements in this section merely provide background information related to the present disclosure. Accordingly, such statements are not intended to constitute an admission of prior art.

Adhesive bandages are used to cover a wound on a patient. A known adhesive bandage includes a portion of the bandage with an adhesive safe for contact with human skin applied thereto. The bandage also includes a portion of the bandage with a fabric or other material intended to rest upon or proximate to a wound on the patient's skin.

Removal of the bandage or checking or cleaning the wound requires one to peel the adhered bandage off the skin of the patient. Some bandages include relatively strong adhesives and are firmly affixed to the skin of the patient. Removing such bandages can be painful or can irritate the skin of the patient. Repeated application and removal of such bandages can damage the skin over time. Other bandages include relatively weak adhesives, reducing pain and irritation caused by removing the bandage, but also increasing a likelihood that the bandage will accidentally fall off or adhere poorly and fail to adequately protect the wound.

SUMMARY

A two-piece bandage is useful for treating wound on a patient. The bandage includes a boundary portion including a bottom surface comprising adhesive for attaching the boundary portion to skin of a patient, an open window in the middle of the boundary portion permitting one to view a wound through the open window, and a top surface. The top surface includes a first portion of the top surface surrounding the open window including a flat surface and a second portion of the top surface including an uneven surface. The bandage further includes a plurality of replaceable wound covering portions, each replaceable wound covering portion comprising a padded section comprising a material to dress the wound. Each replaceable wound covering portion can be sequentially positioned with the padded section proximate to the wound and adhered to the boundary portion. The uneven surface of the second portion is configured to ease removal of each replaceable wound covering portion.

BRIEF DESCRIPTION OF THE DRAWINGS

One or more embodiments will now be described, by way of example, with reference to the accompanying drawings, in which.

DETAILED DESCRIPTION

A two-part bandage is disclosed including a first boundary portion adhered to the skin of the patient and including an open window and a second wound covering portion covering the window and adhering to the boundary portion. A removable, replaceable wound covering portion permits one to dress or treat a wound repeatedly during the healing of the wound without repeatedly pulling the bandage off of the skin of the patient. Further, by using a new wound covering portion each time the portion is removed, sterility of the dressing is improved over a dressing that is simply reapplied to the wound.

Figure 1:
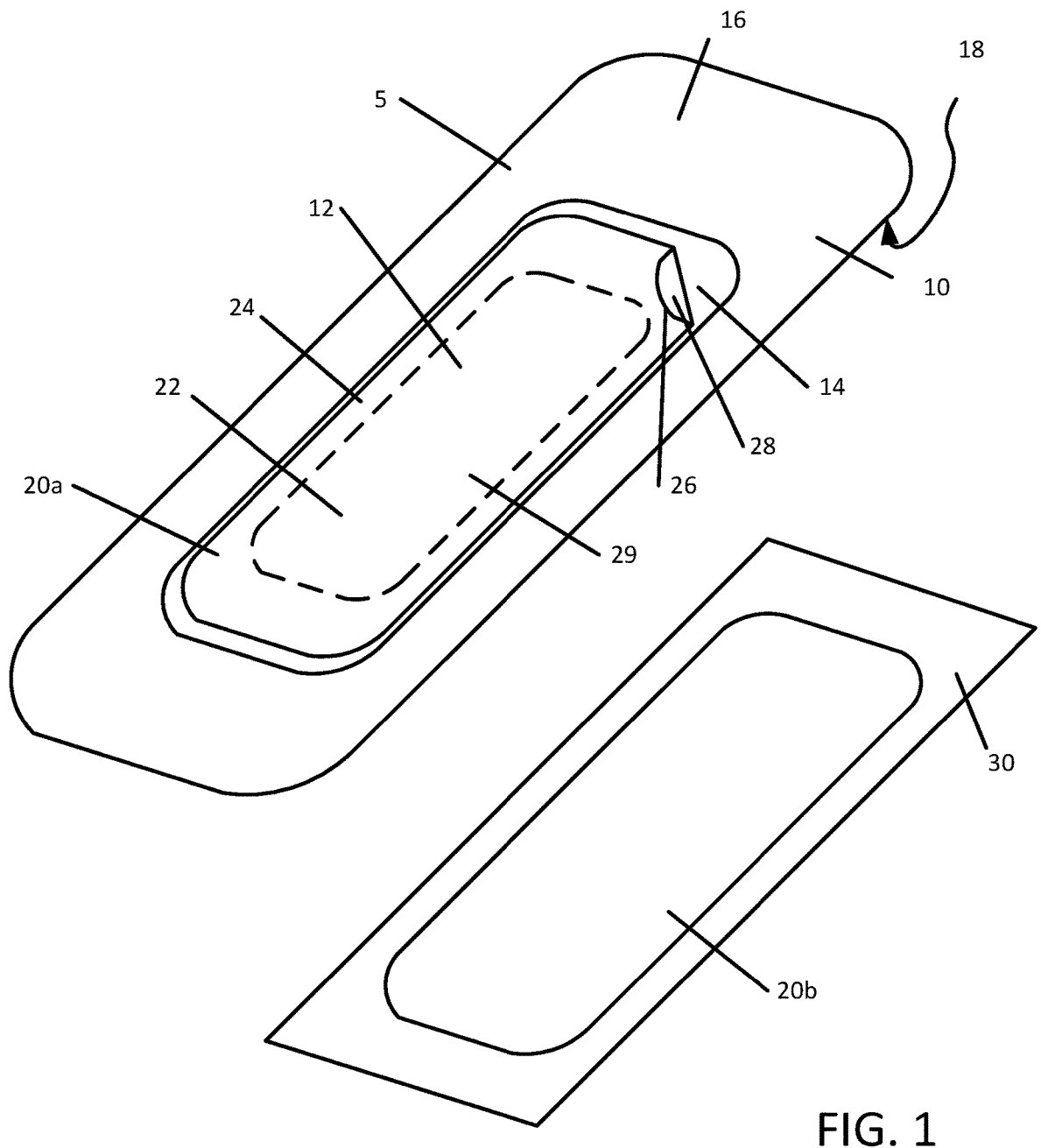
FIG. 1 illustrates an exemplary two-part bandage including a first boundary portion and a second replaceable wound covering portion, in accordance with the present disclosure.

Referring now to the drawings, wherein the showings are for the purpose of illustrating certain exemplary embodiments only and not for the purpose of limiting the same, FIG. 1 illustrates an exemplary two-part bandage including a first boundary portion and a second replaceable wound covering portion. Two-part bandage 5 is illustrated including a first boundary portion 10 and a replaceable wound covering portion 20a. Boundary portion 10 includes a polymerized or cloth based bandage material configured to be adhered to the skin of a patient. Boundary portion 10 has a top surface 16 and a bottom surface 18. Bottom surface 18 includes adhesive configured to temporarily stick to the skin of the patient. The adhesive can include any adhesive used in medical devices known in the art. Boundary portion 10 is configured to be adhered once to the skin of the patient and remain there as long as the patient needs a bandage. Boundary portion 10 includes open window 12, illustrated in FIG. 1 by a dotted line. Open window 12 can be situated over a wound, such that the bottom surface 18 of boundary portion 10 does not come into contact with the wound. Different two-part bandages with different shapes and sizes of open windows can be provided for different wounds. In one exemplary embodiment, the size of the window can be described or printed as an outline upon packaging of the bandages to aid a person providing medical care or first aid to select a correct bandage for a particular wound.

Replaceable wound covering portion 20a is illustrated adhered to top surface 16 of boundary portion 10. Replaceable wound covering portion 20a includes top surface 29 and bottom surface 28. A corner 26 of replaceable wound covering portion 20a is illustrated peeled back from boundary portion 10 to reveal a patch of bottom surface 28. An adhesive is used upon one of bottom surface 28 or patch 14 of top surface 16 to adhere replaceable wound covering portion 20a to boundary portion 10. While such adhesive can be used on either surface, adhesive on bottom surface 28 is advantageous because any fresh replaceable wound covering portion used upon the bandage would have new adhesive that would be unlikely to have been contaminated or made less effective through previous use of the bandage. Exemplary replaceable wound covering portion 20a of FIG. 1 includes a racetrack shaped adhesive coating 24 around a perimeter of bottom surface 28. Coating 24 is shaped such that none of the adhesive or only an incidental amount of adhesive contacts the skin of the patient through window 12. Replaceable wound covering portion 20a includes a padded section 22 located upon bottom surface 28 including gauze or a similar substance known in the art to be placed upon or proximate to or to dress the wound itself. Padded section 22 can be sized to be similar in size to open window 12, such that any skin visible within window 12 will be covered with the gauze material once replaceable wound covering portion 20a is attached to boundary portion 10.

Additionally, a second replaceable wound covering portion 20b is illustrated initially adhered to backing paper 30. Backing paper 30 is known in the art and can include any surface with a coating configured to temporarily hold an object with an adhesive layer and later release that object with the adhesive layer for subsequent adhesion to another object. At any point through the treatment of the patient, replaceable wound covering portion 20a can be removed from bandage 5 and replaced with replaceable wound covering portion 20b. Because replaceable wound covering portion 20a is only adhered to boundary portion 10 or is only slightly adhered to the patient's skin through incidental contact through window 12, removal of replaceable wound covering portion 20a does not irritate the skin of the patient, and a fresh gauze section can be repeatedly provided to the wound without the discomfort of having to pull the adhesive away from the skin of the patient. Boundary portion 10 is removed only at the end of the treatment period. Because boundary portion 10 is only removed once and is not removed and reapplied a number of times, a more aggressive adhesive could be used to keep boundary portion 10 in place throughout the treatment and the skin only has to endure one removal of the adhesive.

Figure 2:
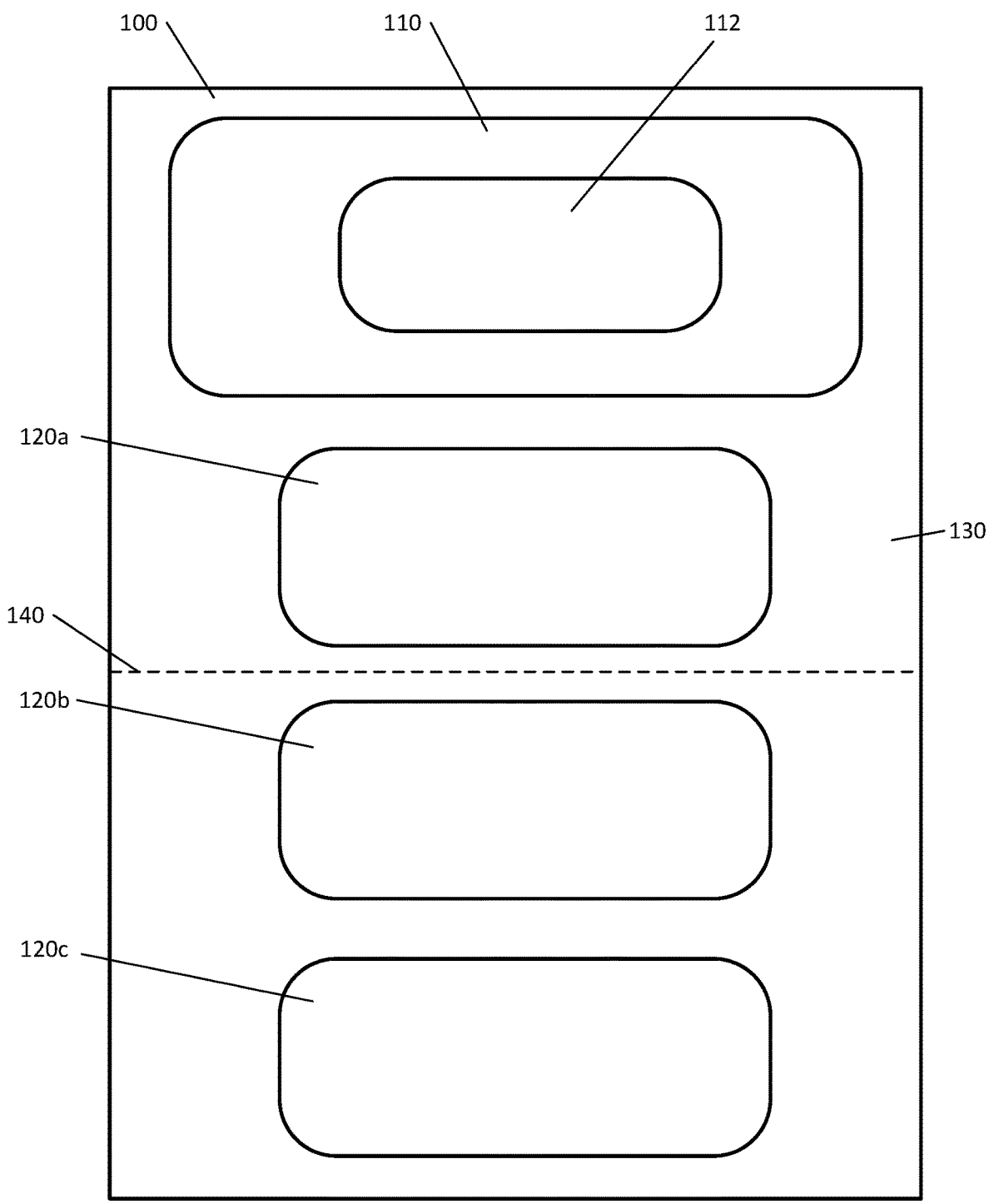
FIG. 2 illustrates a sheet of bandage components that can be supplied or manufactured to include a boundary portion of a two-part bandage and a plurality of replacement wound covering portions, in accordance with the present disclosure.

FIG. 2 illustrates a sheet of bandage components that can be supplied or manufactured to include a boundary portion of a two-part bandage and a plurality of replacement wound covering portions. Sheet 100 is illustrated including backing paper 130, boundary portion 110 and replaceable wound covering portions 120a, 120b, and 120c. Sheet 100 can be provided as a single unit, for example, within a sterile plastic or paper bag. Upon intended use, a person can rip open the package and remove boundary portion 110 from backing paper 130. Boundary portion 110 can be situated to the skin of the patient such that all of a wound on the patient is within open window 112, with adhesive attaching boundary portion 110 to the skin. The person can then place wound covering portion 120a upon boundary portion 110, with adhesive attaching the wound covering portion 120a to the boundary portion. In another embodiment, boundary portion 110 can be provided with one of the replaceable wound covering portions initially already attached to boundary portion 110. Sheet 100 can be retained with the remaining replaceable wound covering portions 120b and 120c still adhered to backing paper 130 for later use when wound covering portion 120a needs to be replaced. In one embodiment, sheet 100 can be perforated in at least one location to permit a portion of backing paper 130 to be removed from the sheet once a portion of the bandage components are removed for use. Exemplary perforation 140 is illustrated.

Figure 3:
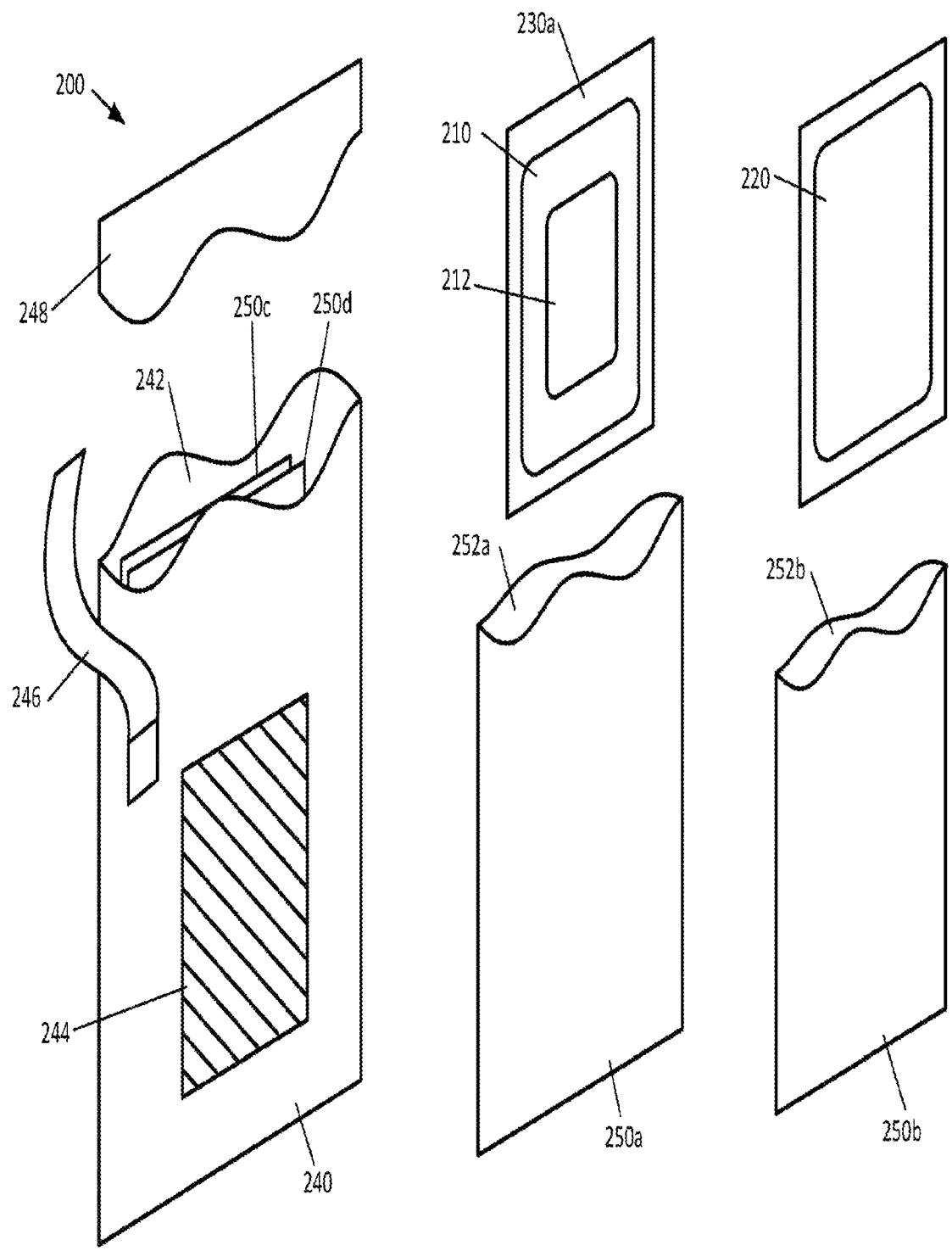
FIG. 3 illustrates exemplary packaging of a two-part bandage providing for individual sterile packaging of each of the components of the bandage and for retention of the packaging close to the patient, in accordance with the present disclosure.

FIG. 3 illustrates exemplary packaging of a two-part bandage providing for individual sterile packaging of each of the components of the bandage and for retention of the packaging close to the patient. Two-part bandage unit 200 is illustrated including two-part bandage packaging 240. Two-part bandage packaging 240 includes a paper, plastic, or other material envelope, box, or other container that can initially hold individually wrapped bandage components. In the example of FIG. 3, packaging 240 has been torn open with removed top 248 discarded. Component packaging 250a and 250b have been removed and include paper or other similar packaging initially holding boundary portion 210 and replaceable wound covering portion 220, respectively. Packaging 250a and 250b have both been removed from packaging 240 and opened to remove boundary portion 210 and replaceable wound covering portion 220, respectively, from cavities 252a and 252b, respectively. Boundary portion 210 can subsequently be removed from backing paper 230a and situated to a wound by locating the wound to open window 212. Replaceable wound covering portion 220 can then be adhered to boundary portion 210. In another embodiment, replaceable wound covering portion 220 could be provided already attached to boundary portion 210. Component packaging 250c and 250d remain within cavity 242 of packaging 240 still retained in an unopened state and each can contain one or more replaceable wound covering portions. As the patient needs a replaceable wound covering portion replaced, one of the component packaging 250c or 250d can be removed and opened.

Packaging 240 is provided with optional adhesive section 244 and tether 246 for attaching packaging 240 to a patient's hospital bed, end table, or any other convenient location such that the packaging 250c and 250d can be accessed as needed. Adhesive section 244 can come with backing paper initially attached. Tether 246 can include adhesive, a pair of snap features, or any other mechanism known in the art for temporarily attaching a tether to an object.

In some embodiments of the disclosure, the outer perimeter of a replaceable wound covering portion can be smaller than the outer perimeter of the matching boundary portion. In the example of FIG. 3, replaceable wound covering portion 220 is illustrated to include the same size outer perimeter as boundary portion 210. This can aid in easily aligning the portions and ensuring that any gauze attached to wound covering portion 220 is properly aligned to window 212.

Figure 4:
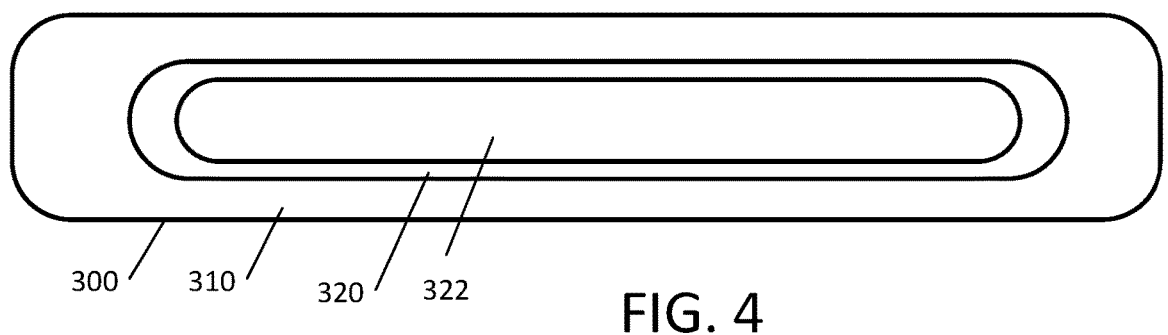
FIG. 4 illustrates an exemplary two-part bandage configured to be applied to a long narrow wound such as a surgical incision, in accordance with the present disclosure.

FIG. 4 illustrates an exemplary two-part bandage configured to be applied to a long narrow wound such as a surgical incision. Two-part bandage 300 is illustrated and includes boundary portion 310 and replaceable wound covering portion 320. Boundary portion 310 includes a long narrow open window to permit one to view a long incision, possibly including stitches or other medical applications to close the wound. Raised padding portion 322 is visible upon wound covering portion 320. Depending upon the thickness and rigidity of the material used for wound covering portion 320 and the thickness of the padding material used, such as gauze, the raised padding portion 322 may or may not be evident on a bandage.

Figure 5:
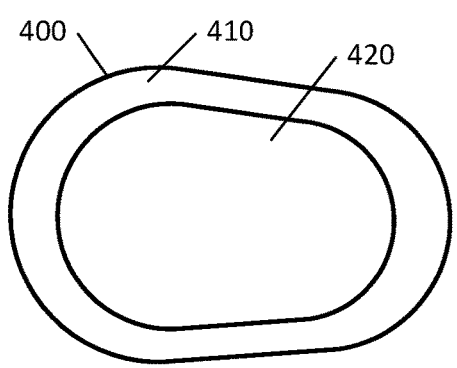
FIG. 5 illustrates an exemplary two-part bandage configured to be applied around a patient's eye, in accordance with the present disclosure.

FIG. 5 illustrates an exemplary two-part bandage configured to be applied around a patient's eye. Two-part bandage 400 includes boundary portion 410 and wound covering portion 420 applied thereto. Boundary portion 410 includes an open window sized to permit one to view the eye within the window. In the exemplary embodiment of FIG. 5, no raised padded section is evident due to a thicker material being used for portion 420, a thinner gauze material being used for the padding, or both. A number of different shapes and sizes of two-piece bandages are envisioned, and the disclosure is not intended to be limited to the examples provided herein.

Figure 6:
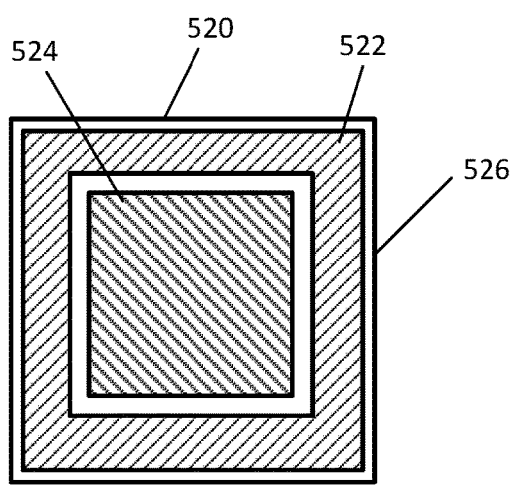
FIG. 6 illustrates an exemplary bottom side of a replaceable wound covering portion, in accordance with the present disclosure.

FIG. 6 illustrates an exemplary bottom side of a replaceable wound covering portion. Replaceable wound covering portion 520 includes a square-shaped perimeter 526, a padded portion 524 to be placed proximate to a wound, and an adhesive portion 522 configured to attach the wound covering portion to a matching boundary portion. In some embodiments, because the adhesive used on adhesive portion 522 is going to be attached to a boundary portion and not to the skin of the patient, a more aggressive adhesive can be used than would be used on a directly applied bandage. In this way, adhesive portion 522 in some embodiments can be smaller or have less surface area than a typical directly applied bandage.

Figure 7:
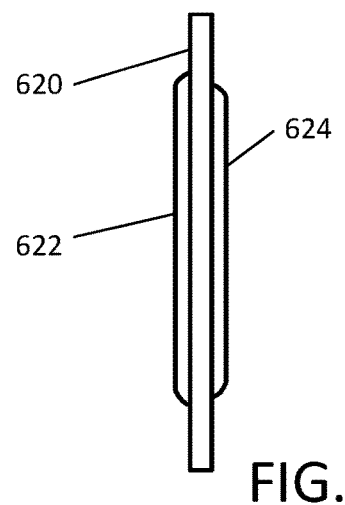
FIG. 7 illustrates an exemplary replaceable wound covering portion in profile including a thin padded section, in accordance with the present disclosure.
Figure 8:
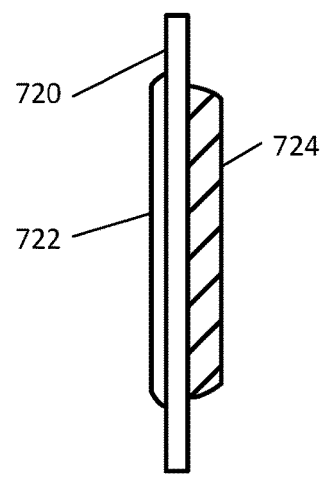
FIG. 8 illustrates another exemplary replaceable wound covering portion in profile including a thick padded section, in accordance with the present disclosure.

FIG. 7 illustrates an exemplary replaceable wound covering portion in profile. Replaceable wound covering portion 620 includes raised padding portion 622 and padded section 624. Padded section 624 can include any number of wound covering materials known in the art and can include an absorbent material, a coating or membrane configured to prevent clotted blood from sticking to the padding, medication or a treated coating, and any other materials or substances known in the art for use upon a bandage applied to a wound. FIG. 8 illustrates another exemplary replaceable wound covering portion in profile. Replaceable wound covering portion 720 includes raised padding portion 722 and padded section 724. Padded section 724 is thicker and can be more absorbent, for example, so that a medicated liquid can be applied to the bandage. In this way, timed or scheduled replacement of the wound covering portions can be used according to a treatment plan to periodically apply a medicated liquid, powder, or ointment to the wound.

Figure 9:
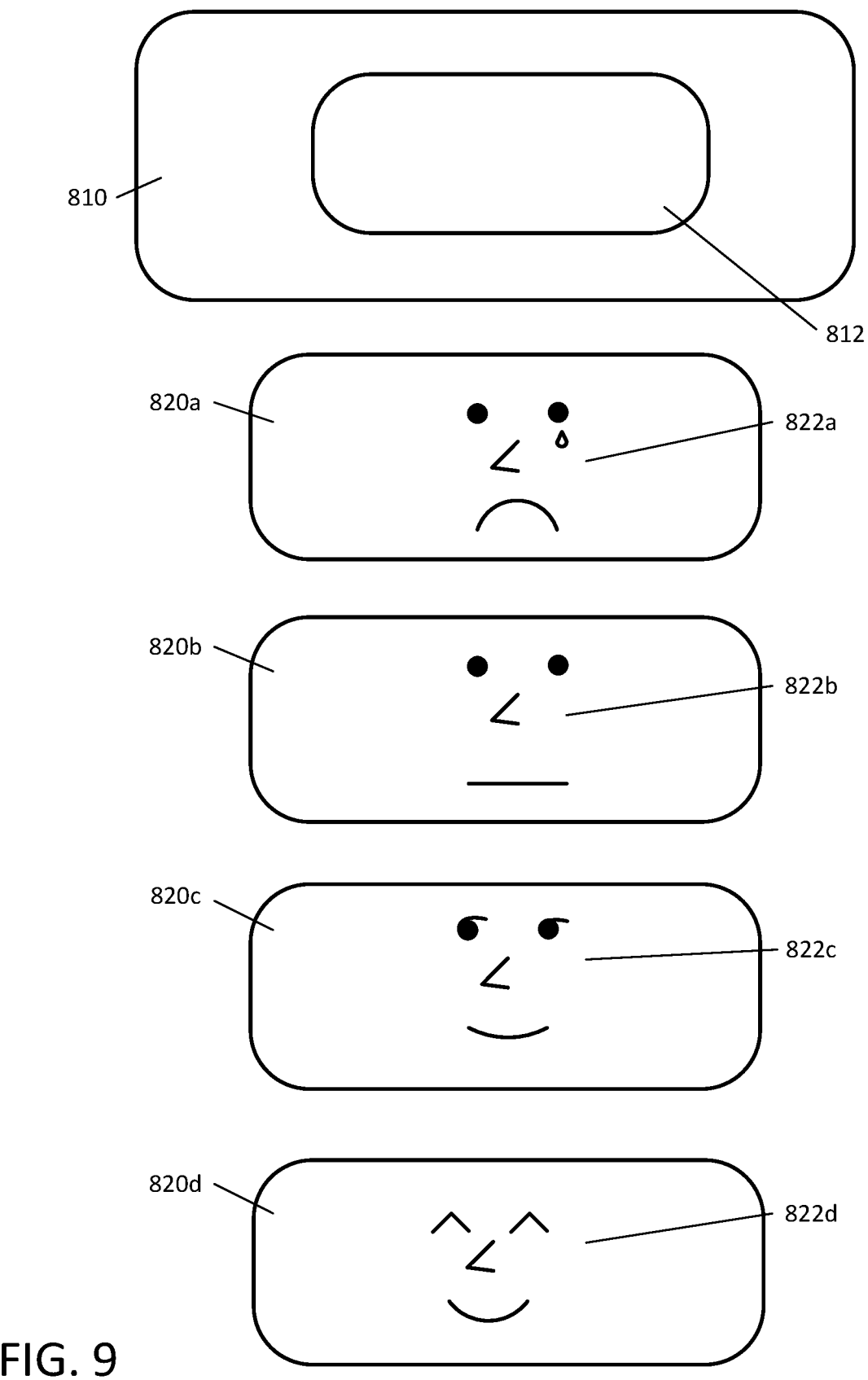
FIG. 9 illustrates and exemplary two-part bandage including a plurality of replaceable wound covering portions, each of the wound covering portions including different graphic patterns upon a top surface, in accordance with the present disclosure.

FIG. 9 illustrates and exemplary two-part bandage including a plurality of replaceable wound covering portions, each of the wound covering portions including different graphic patterns upon a top surface. Boundary portion 810 is illustrated including open window 812. Replaceable wound covering portions 820a, 820b, 820c, and 820d are illustrated, each including a respective graphic pattern 822a, 822b, 822c, and 822d imprinted thereupon. A number of exemplary graphic patterns are envisioned. For example, three different colors can be used, for example, indicating a shift in a hospital in which the wound covering portion was last replaced. In this way, a medical professional could easily audit a floor to make sure that all bandages had been updated for a particular shift. In another example, a doctor could have a range of wound covering portions to select from, each of a set of patterns, for example, including a letter designation, indicating an evaluation of how well the wound was healing or if there was any sign of infection. In the exemplary embodiment of FIG. 9, graphic patterns 822a, 822b, 822c, and 822d include a progression of facial expressions, which could be used, for example, to encourage a younger patient through a healing time, first, to sympathize with the patient after an injury or procedure, and, later, to remind the patient that happier times are on the way as the wound heals. A number of exemplary graphic patterns are envisioned, and the disclosure is not intended to be limited to the examples provided herein.

Figure 10:
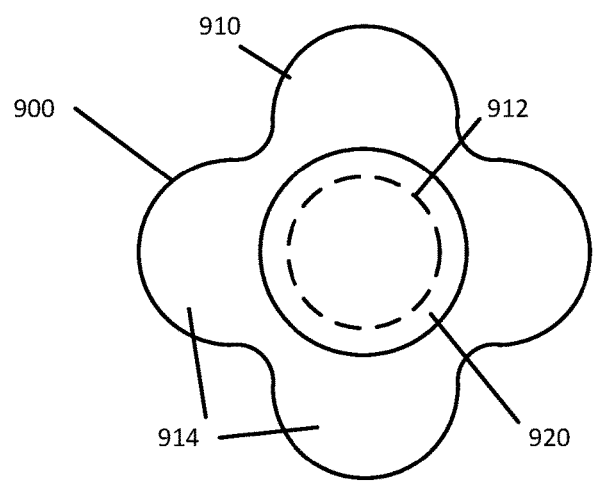
FIG. 10 illustrates an exemplary bandage for use on a knee or elbow including the disclosed wound covering portion, in accordance with the present disclosure.

A wide variety of bandages can include boundary portions and wound covering portions as disclosed herein. FIG. 10 illustrates an exemplary bandage for use on a knee or elbow including the disclosed wound covering portion. Bandage 900 is illustrated including boundary portion 910 and wound covering portion 920 adhered thereto. Boundary portion 910 includes treatment window 912 and four wing panels 914. Wing panels 914 increase adhesive contact between boundary portion 910 and the skin of the patient, thereby increasing a likelihood that the bandage will remain in place on a articulating body part such as a knee or elbow.

Figure 11:
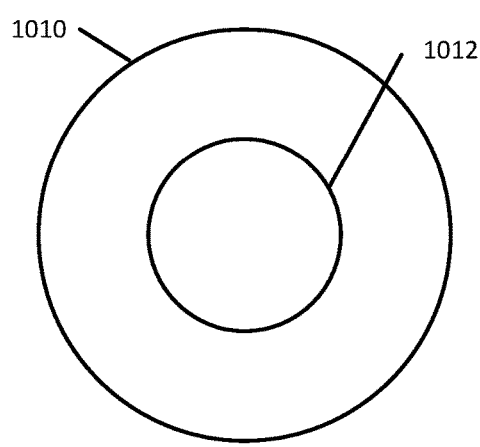
FIG. 11 illustrates an exemplary boundary portion of a bandage for use on a intravenous injection site or mole removal site, in accordance with the present disclosure.

FIG. 11 illustrates an exemplary boundary portion of a bandage for use on a intravenous injection site or mole removal site. Round boundary portion 1010 includes a round window 1012.

Figure 12:
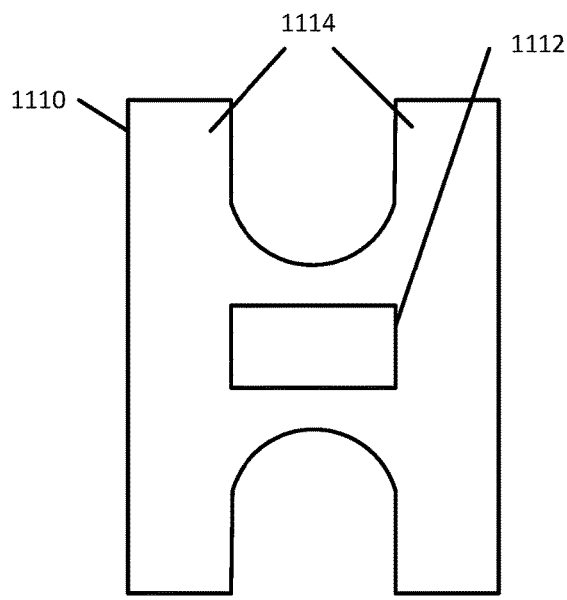
FIG. 12 illustrates an exemplary boundary portion of a bandage for use on a knuckle, elbow, or knee, in accordance with the present disclosure.

FIG. 12 illustrates an exemplary boundary portion of a bandage for use on a knuckle, elbow, or knee. H-shaped boundary portion 1110 includes window 1112 and leg portions 1114.

Figure 13:
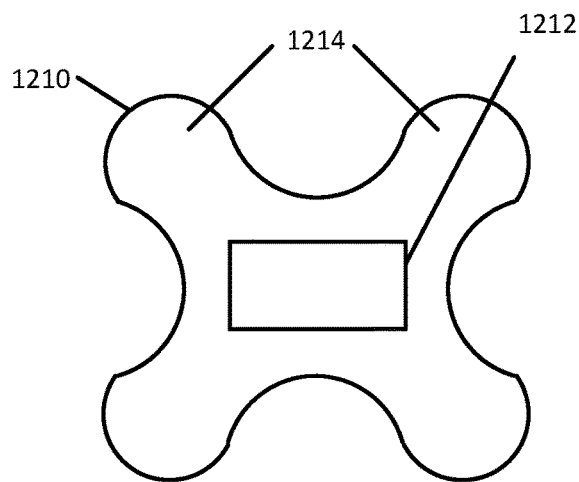
FIG. 13 illustrates an additional exemplary boundary portion of a bandage for use on a a knuckle, elbow, or knee, in accordance with the present disclosure.

FIG. 13 illustrates an additional exemplary boundary portion of a bandage for use on a a knuckle, elbow, or knee. X-shaped boundary portion 1210 includes window 1212 and leg portions 1214.

Figure 14:
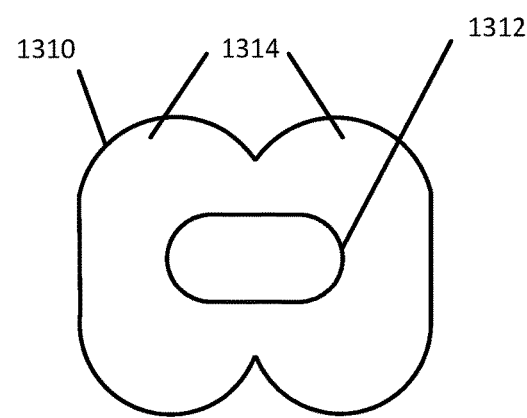
FIG. 14 illustrates an exemplary boundary portion of a bandage for use on a fingertip, in accordance with the present disclosure.

FIG. 14 illustrates an exemplary boundary portion of a bandage for use on a fingertip. Four-lobe boundary portion 1310 includes window 1312 and four lobe portions 1314.

Figure 15:
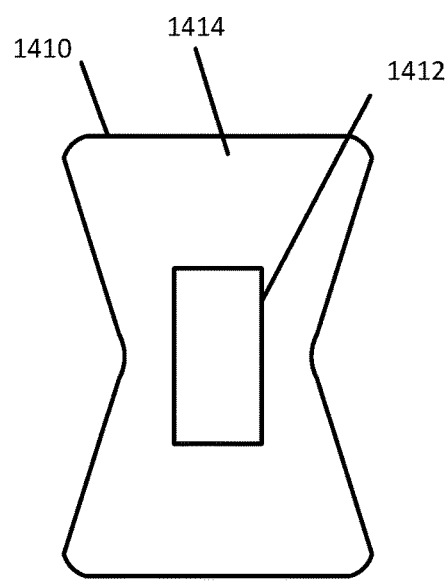
FIG. 15 illustrates an exemplary boundary portion of a bandage for use on a knuckle, in accordance with the present disclosure.

FIG. 15 illustrates an exemplary boundary portion of a bandage for use on a knuckle. Double-taper boundary portion 1410 includes window 1412 and widening end portions 1414.

Figure 16:
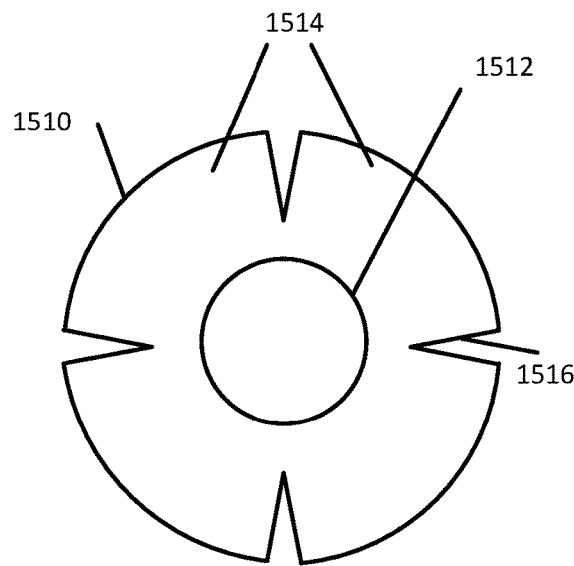
FIG. 16 illustrates an exemplary boundary portion of a bandage for use on a shoulder, arm pit, or knee, in accordance with the present disclosure.

FIG. 16 illustrates an exemplary boundary portion of a bandage for use on a shoulder, arm pit, or knee. Relief-cut round boundary portion 1510 includes window 1512, round cut extending portions 1514, and relief cuts 1516.

Figure 17:
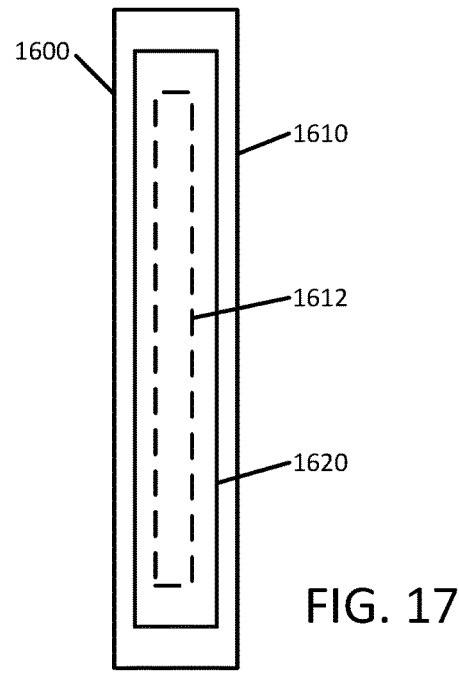
FIG. 17 illustrates an exemplary bandage configured to be applied to an incision wound, for example, a surgical site, in accordance with the present disclosure.

FIG. 17 illustrates an exemplary bandage configured to be applied to an incision wound, for example, a surgical site. Bandage 1600 is illustrated including boundary portion 1610 and wound covering portion 1620. Boundary portion 1610 includes wound treatment window 1612. In order to cover a long, thin incision wound site, the boundary portion and the corresponding window can each have high aspect ratios, with thin widths and long lengths. Non-limiting examples of boundary portions can have aspect ratios of 5:1, 10:1, or 20:1. The provided boundary portion shapes and proportions, window shapes and proportions, and wound covering portion shapes and proportions are provide as non-limiting examples, and the disclosure is not intended to be limited to the particular examples provided.

Figure 18:
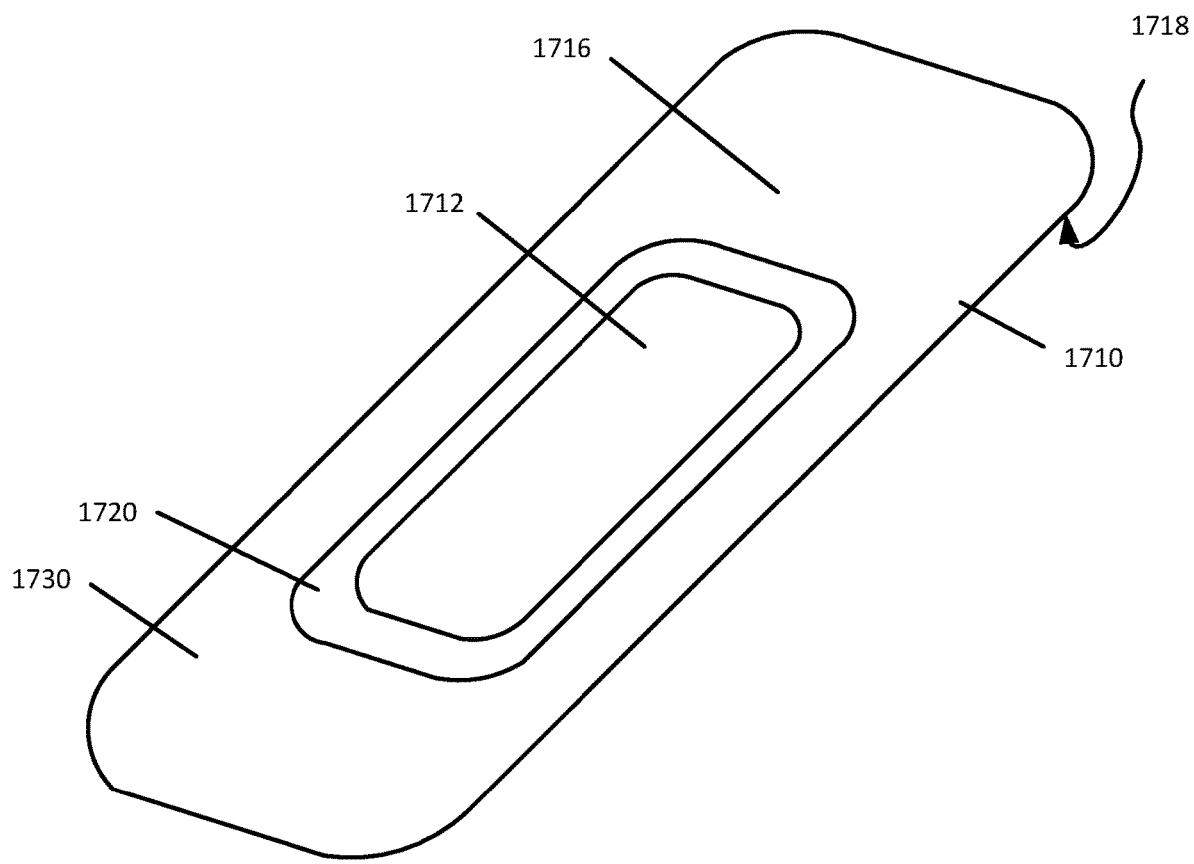
FIG. 18 illustrates an exemplary bandage including a boundary portion similar to the boundary portion of FIG. 1, the boundary portion of FIG. 18 including a top surface including a first smooth surface portion of the top surface surrounding an open window for attachment of a replaceable wound covering portion, the first portion enabling sterile encapsulation of the open window, and a second uneven surface portion of the top surface making removal of the replaceable wound covering portion easier than if the second portion were a smooth surface, in accordance with the present disclosure.

FIG. 18 illustrates an exemplary bandage including a boundary portion similar to the boundary portion of FIG. 1, the boundary portion of FIG. 18 including a top surface including a first smooth surface portion of the top surface surrounding an open window for attachment of a replaceable wound covering portion, the first portion enabling sterile encapsulation of the open window, and a second uneven surface portion of the top surface making removal of the replaceable wound covering portion easier than if the second portion were a smooth surface. Boundary portion 1710 includes a polymerized or cloth based bandage material configured to be adhered to the skin of a patient. Boundary portion 1710 has a top surface 1716 and a bottom surface 1718. Bottom surface 1718 includes adhesive configured to temporarily stick to the skin of the patient. The adhesive can include any adhesive used in medical devices known in the art. Boundary portion 1710 is configured to be adhered once to the skin of the patient and remain there as long as the patient needs a bandage. Boundary portion 1710 includes open window 1712. Open window 1712 can be situated over a wound, such that the bottom surface 1718 of boundary portion 1710 does not come into contact with the wound. A replaceable wound covering portion is separately provided to be adhered to top surface 1716 of boundary portion 1710. An adhesive is used upon one of a bottom surface of the replaceable wound covering portion or upon top surface 1716 to adhere the replaceable wound covering portion to boundary portion 1710. While such adhesive can be used on either surface, adhesive on the bottom surface of the replaceable wound covering portion is advantageous because any fresh replaceable wound covering portion used upon the bandage would have new adhesive that would be unlikely to have been contaminated or made less effective through previous use of the bandage.

Skin with a wound upon it can be sensitive. Removing one item adhered to another item includes forces applied to both items to cause separation of the adhesive. Skin of the patient benefits from a bandage encapsulating a wound in a sterile environment, while the skin of the patient also benefits from being held as still as possible without being stretched or strained by removal of bandages and the required separation forces involved in breaking the adhesive seal. An improved bandage is provided, including a boundary portion of FIG. 18 including top surface 1716 including first smooth surface portion 1720 of the top surface surrounding open window 1712 for attachment of a replaceable wound covering portion, first portion 1720 enabling sterile encapsulation of the open window 1712, and second uneven surface portion 1730 of the top surface making removal of the replaceable wound covering portion easier than if the second portion were a smooth surface.

When replaceable wound covering portion 20a of FIG. 1 is adhered to top surface 1716 of FIG. 18, the replaceable wound covering portion adheres firmly to first portion 1720 and adheres loosely to second portion 1730. A person removing the replaceable wound covering portion from boundary portion 1710 can easily remove an outer portion of the replaceable wound covering portion adhered to portion 1730, with only the portion of the replaceable wound covering portion adhered to first portion 1720 requiring significant force to remove.

Figure 19:
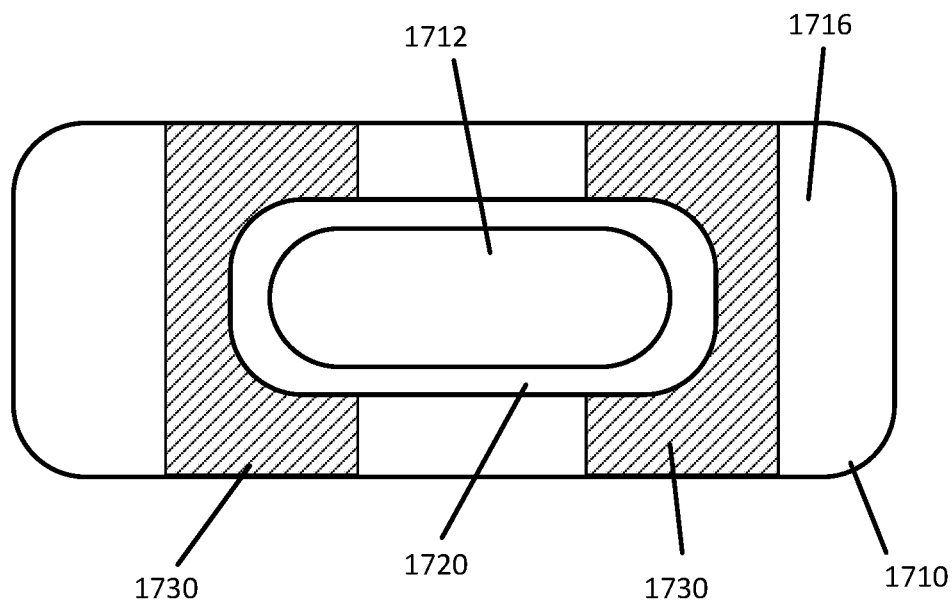
FIG. 19 illustrates an exemplary embodiment of the bandage of FIG. 18, wherein the second portion comprises at least one area of the top surface proximate to one of distal end of the open window, in accordance with the present disclosure.

FIG. 19 illustrates an exemplary embodiment of the bandage of FIG. 18, wherein the second portion comprises at least one area of the top surface proximate to one of distal end of the open window. Boundary portion 1710 is illustrated, including first portion 1720 of top surface 1716 including a flat surface surrounding open window 1712. Additionally, two second portions 1730 including uneven surfaces are illustrated. The uneven surface of portions 1730 is configured to make adhesion of a replaceable wound covering portion to portion 1730 less effective, thereby making removal of the replaceable wound covering portion easier than it would be if portion 1730 were flat. In the embodiment of FIG. 19, the two second portions 1730 do not cover an entirety of the top surface of the bandage outside of first portion 1720.

Figure 20:
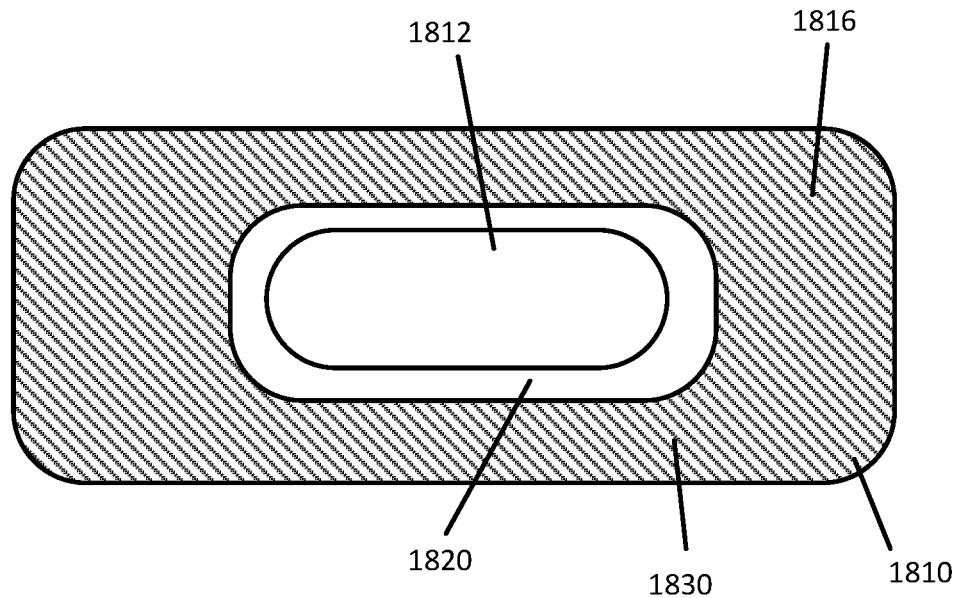
FIG. 20 illustrates an alternative embodiment of the bandage of FIG. 18, wherein the first portion and the second portion together cover an entirety of the top surface, in accordance with the present disclosure.

FIG. 20 illustrates an alternative embodiment of the bandage of FIG. 18, wherein the first portion and the second portion together cover an entirety of the top surface. Boundary portion 1810 includes open window 1812 surround by a first portion 1820 of top surface 1816 including a flat surface. Boundary portion 1810 is similar to boundary portion 1710 of FIG. 19, except that second portion 1830 including an uneven surface includes all of top surface 1816 not including first portion 1820.

Figure 21:
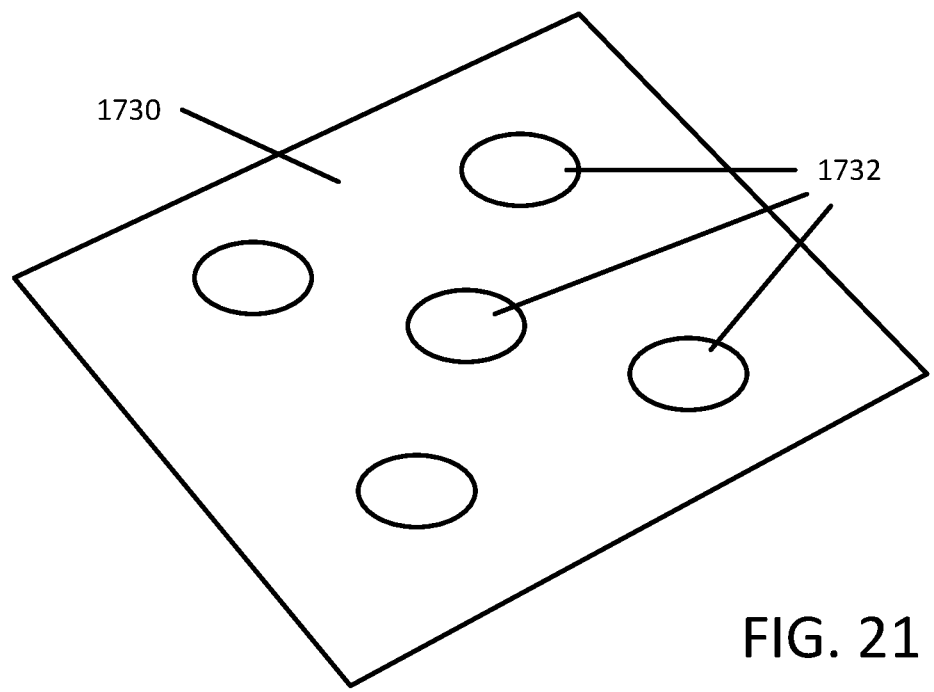
FIG. 21 illustrates in perspective view in magnified detail for clarity an exemplary uneven surface of the second portion of FIG. 18, with spaced raised bumps causing the surface to be uneven, in accordance with the present disclosure.
Figure 22:
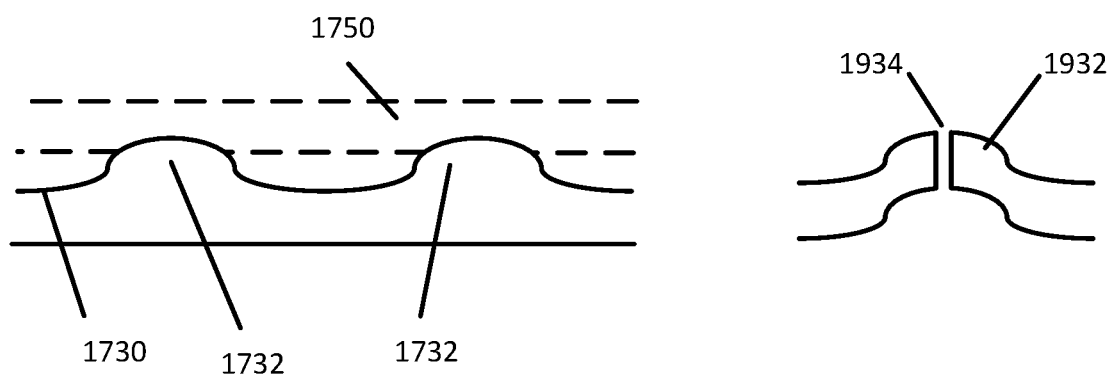
FIG. 22 illustrates in side sectional view an exemplary cross-section of the uneven surface of FIG. 21, with the bumps comprising solid material rising above a generally flat surface of the bandage, in accordance with the present disclosure.

FIG. 21 illustrates in perspective view in magnified detail for clarity an exemplary uneven surface of the second portion of FIG. 18, with spaced raised bumps causing the surface to be uneven. A small section of second portion 1730 is illustrated, including a plurality of exemplary raised bumps 1732 configured to made adhesion of a replaceable wound covering portion less effective than if the surface were flat. FIG. 22 illustrates in side sectional view an exemplary cross-section of the uneven surface of FIG. 21, with the bumps comprising solid material rising above a generally flat surface of the bandage. Second portion 1730 is illustrated, including two exemplary raised bumps 1732. An exemplary replaceable wound covering portion 1750 is illustrated with dotted lines, the replaceable wound covering portion 1750 connecting and adhering to the tops of bumps 1732 without connecting with the surface of second portion 1730 between bumps 1732. By reducing the surface area that replaceable wound covering portion 1750 is connected to second portion 1730, the force necessary to remove replaceable wound covering portion 1750 from second portion 1730 is smaller than if an entirety of the two surfaces were connected to each other.

Figure 23:
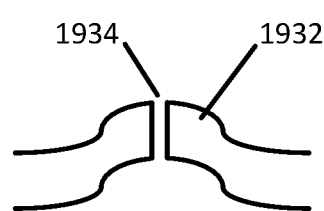
FIG. 23 illustrates in side sectional view an alternative exemplary cross-section of the uneven surface of FIG. 21, with the bumps comprising substantially uniform thickness material in the bandage and with an exemplary through hole formed in the bump, in accordance with the present disclosure.

FIG. 23 illustrates in side sectional view an alternative exemplary cross-section of the uneven surface of FIG. 21, with a bump comprising substantially uniform thickness material in the bandage and with an exemplary through hole formed in the bump. Bump 1932 is illustrated, wherein the material of the boundary portion is deformed or formed with an upward bend, such that the bump 1932 is elevated above surrounding material. Additionally, an optional hole 1934 is illustrated, providing for air to pass through the material and promote skin health beneath the bandage.

Figure 24:
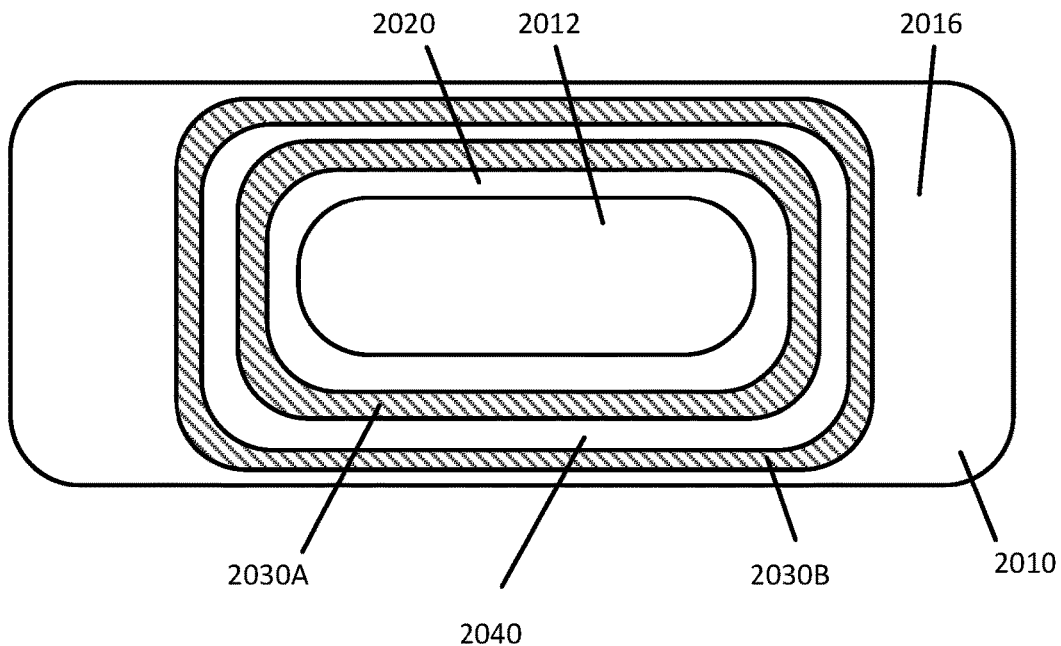
FIG. 24 illustrates a bandage similar to the bandages of FIGS. 18 and 21, with an alternative second uneven surface portion including a series of raised ridges on the surface of the bandage, in accordance with the present disclosure.

FIG. 24 illustrates a bandage similar to the bandages of FIGS. 18 and 21, with an alternative second uneven surface portion including a series of raised ridges on the surface of the bandage. Boundary portion 2010 is illustrated, including open window 2012, first portion 2020 of top surface 2016 including a flat surface, and second portions 2030A and 2030B of top surface 2016 including a plurality of exemplary raised concentric rings being formed upon top surface 2016, with a lower portion 2040 between the rings causing the surface to be uneven. For the same reasons as described in relation to FIGS. 21-23, the uneven surface of second portions 2030A and 2030B cause an attached replaceable wound covering portion to adhere to top surface 2016 less strongly than if the surface were flat.

Figure 25:
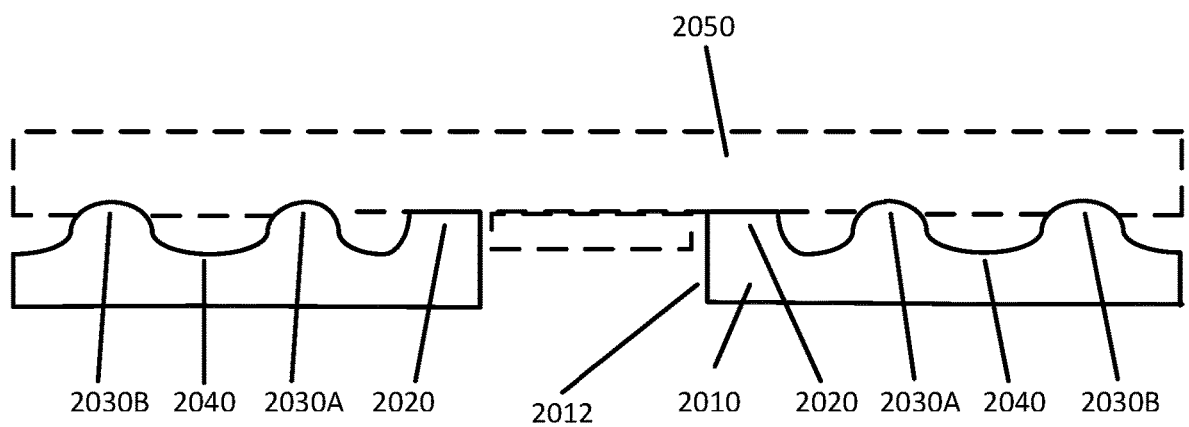
FIG. 25 illustrates the bandage of FIG. 24 in side sectional view, illustrating the first portion, the second portion, and the open window, in accordance with the present disclosure.

FIG. 25 illustrates the bandage of FIG. 24 in side sectional view, illustrating the first portion, the second portion, and the open window. Boundary portion 2010 is illustrated, including open window 2012, first portion 2020, second portion 2030A and 2030B comprising a plurality of raised rings, and lower portion 2040 between the raised rings. Additionally, replaceable wound covering portion 2050 including a pad covering the open window 2012 is illustrated with dotted lines. The raised ridges including rings of FIGS. 24 and 25 can be replaced with exemplary parallel ridges to a similar effect.

Bumps, raised ridges formed in concentric rings or parallel lines, or other similar structures can all be used as described herein to cause a portion of the top surface of a boundary portion of a bandage as disclosed herein to adhere weakly to a neighboring replaceable wound covering portion. Non-limiting examples of such structures are provided herein, while other similar structures are envisioned.

The disclosure has described certain preferred embodiments and modifications of those embodiments. Further modifications and alterations may occur to others upon reading and understanding the specification. Therefore, it is intended that the disclosure not be limited to the particular embodiment(s) disclosed as the best mode contemplated for carrying out this disclosure, but that the disclosure will include all embodiments falling within the scope of the appended claims.

The invention claimed is:

1. An apparatus comprising a two-piece bandage, comprising:
   a boundary portion comprising:
      a bottom surface comprising adhesive for attaching the boundary portion to skin of a patient;
      an open window in a middle of the boundary portion permitting one to view a wound through the open window; and
      a top surface comprising:
         a first portion of the top surface surrounding the open window including a flat surface, wherein the first portion is immediately adjacent the open window; and
         a second portion of the top surface being an uneven surface, wherein the second portion surrounds the first portion, wherein the second portion of the top surface comprises raised bumps, wherein the raised bumps comprise through holes configured to permit air to pass through the bandage; and
   a plurality of replaceable wound covering portions, each replaceable wound covering portion comprising a padded section comprising a material to dress the wound; and
   wherein each replaceable wound covering portion can be sequentially positioned with the padded section proximate to the wound and adhered to the boundary portion; and
   wherein the uneven surface of the second portion is configured to ease removal of each replaceable wound covering portion.

2. The apparatus of claim 1, wherein the first portion and the second portion collectively cover an entirety of the top surface.

3. The apparatus of claim 1, wherein the first portion and the second portion collectively cover a fraction of an area of the top surface.

4. The apparatus of claim 1, wherein the raised bumps are a plurality of spaced protrusions.

5. An apparatus comprising a two-piece bandage, comprising:
   a boundary portion comprising:
      a bottom surface comprising adhesive for attaching the boundary portion to skin of a patient;
      an open window in a middle of the boundary portion permitting one to view a wound through the open window; and a top surface comprising:
- a first portion of the top surface surrounding the open window including a flat surface, wherein the first portion is immediately adjacent the open window; and
- a second portion of the top surface being an uneven surface, wherein the second portion surrounds the first portion, wherein the second portion of the top surface comprises raised ridges wherein the raised ridges comprise concentric rings formed around the first portion of the top surface; and a plurality of replaceable wound covering portions, each replaceable wound covering portion comprising a padded section comprising a material to dress the wound; and wherein each replaceable wound covering portion can be sequentially positioned with the padded section proximate to the wound and adhered to the boundary portion; and wherein the uneven surface of the second portion is configured to ease removal of each replaceable wound covering portion.

* * * * *